US011602292B2

United States Patent
Crane et al.

(10) Patent No.: US 11,602,292 B2
(45) Date of Patent: *Mar. 14, 2023

(54) SENSOR CALIBRATION

(71) Applicants: Baxter International Inc., Deerfield, IL (US); Baxter Healthcare SA, Glattpark (CH)

(72) Inventors: Barry Colin Crane, Oxfordshire (GB); Nicholas Paul Barwell, Oxfordshire (GB); William Paterson, Oxfordshire (GB); Robert Perkins, Abingdon (GB)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 750 days.

This patent is subject to a terminal disclaimer.

(21) Appl. No.: 16/592,266

(22) Filed: Oct. 3, 2019

(65) Prior Publication Data

US 2020/0054254 A1    Feb. 20, 2020

Related U.S. Application Data

(63) Continuation of application No. 15/115,967, filed as application No. PCT/GB2015/050283 on Feb. 3, 2015, now Pat. No. 10,433,778.

(30) Foreign Application Priority Data

Feb. 4, 2014   (GB) ...................... 1401878

(51) Int. Cl.
*A61B 5/1495*   (2006.01)
*A61B 5/1459*   (2006.01)
*A61B 5/145*   (2006.01)

(52) U.S. Cl.
CPC .......... *A61B 5/1495* (2013.01); *A61B 5/1459* (2013.01); *A61B 5/14532* (2013.01); *A61B 2560/0233* (2013.01)

(58) Field of Classification Search
CPC . A61B 5/1459; A61B 5/1495; A61B 5/14532; A61B 2560/0233
See application file for complete search history.

(56) References Cited

U.S. PATENT DOCUMENTS 3,202,273 A    8/1965   Riall
4,475,914 A    10/1984  Portnoff
(Continued)

FOREIGN PATENT DOCUMENTS

DE    19546535    6/1997
JP    61270650    11/1986
(Continued)

OTHER PUBLICATIONS

"Sterilization Methods Stand the Test of Time". Hemmerich KJ, Masefield J, Nelson JR. Medical Device and Diagnostic Industry. 2004. Source URL: https://www.mddionline.com/sterilization/sterilization-methods-stand-test-time. Accessed Jul. 1, 2022 (Year: 2004).*

(Continued)

*Primary Examiner* — Christine H Matthews
*Assistant Examiner* — Joshua Daryl D Lannu
(74) *Attorney, Agent, or Firm* — K&L Gates LLP

(57) ABSTRACT

A process for calibrating a glucose sensor under sterile conditions includes providing separate, sterile, glucose-containing calibration fluids, each having a different glucose concentration, and in turn providing these fluids to a sensing zone containing a sensing probe of a glucose sensor. Each solution is typically, in turn, propelled into the sensing zone, thus flushing out used fluid already present in the sensing (Continued)

zone. The process provides rapid calibration of a glucose sensor in a sterile fashion and is therefore appropriate for point-of-use calibration.

6 Claims, 4 Drawing Sheets

(56) References Cited

U.S. PATENT DOCUMENTS

| | | | |
|---|---|---|---|
| 4,689,308 | A | 8/1987 | Gerhard |
| 5,114,859 | A | 5/1992 | Kagenow |
| 5,156,972 | A | 10/1992 | Issachar |
| 5,188,803 | A | 2/1993 | Hochberg |
| 5,208,147 | A | 5/1993 | Kagenow et al. |
| 5,992,211 | A | 11/1999 | Skrtic |
| 6,037,178 | A | 3/2000 | Leiner et al. |
| 6,387,672 | B1 | 5/2002 | Arimori et al. |
| 7,785,535 | B2 | 8/2010 | Chen et al. |
| 2003/0224523 | A1 | 12/2003 | Thornberg et al. |
| 2004/0126766 | A1 | 7/2004 | Amorese |
| 2006/0108218 | A1 | 5/2006 | Gephart et al. |
| 2008/0188722 | A1* | 8/2008 | Markle .......... G01N 33/66 600/316 |
| 2008/0312518 | A1 | 12/2008 | Jina et al. |
| 2009/0018426 | A1* | 1/2009 | Markle .......... G01N 27/3274 73/1.02 |
| 2011/0154880 | A1* | 6/2011 | Petisce .......... G01N 33/96 73/1.03 |
| 2012/0096918 | A1* | 4/2012 | Crane .......... A61B 5/1495 73/1.02 |
| 2012/0240656 | A1 | 9/2012 | Crane et al. |
| 2013/0266478 | A1 | 10/2013 | Crane et al. |

FOREIGN PATENT DOCUMENTS

| | | |
|---|---|---|
| JP | 63247646 | 10/1988 |
| WO | 85/04719 | 10/1985 |
| WO | 90/02938 | 3/1990 |
| WO | 93/03362 | 2/1993 |
| WO | 94/19683 | 9/1994 |
| WO | 01/67079 | 9/2001 |
| WO | 2008/001091 | 1/2008 |
| WO | 2008/141243 | 11/2008 |
| WO | 2012/095628 | 7/2012 |
| WO | 2012/164268 | 12/2012 |

OTHER PUBLICATIONS

International Search Report and Written Opinion for Related International Application No. PCT/GB2015/050283; report dated Apr. 21, 2015; (12 pages).
Search Report for related Application No. GB1401878.2; report dated Aug. 22, 2014; (1 page).
European Office Action for related European Application No. 15704080.9; action dated Dec. 19, 2019; (5 pages).
International Search Report and Written Opinion for related International Application No. PCT/GB2015/050283; report dated Apr. 21, 2015; (8 pages).

* cited by examiner

SENSOR CALIBRATION

PRIORITY CLAIM AND CROSS-REFERENCE TO RELATED APPLICATIONS

This application is a continuation of U.S. patent application Ser. No. 15/115,967, filed Aug. 2, 2016, which is a National Stage application under 35 U.S.C. § 371 of International Application No. PCT/GB2015/050283, filed Feb. 3, 2015, which claims the benefit of priority to GB 1401878.2, filed Feb. 4, 2014. The disclosure of the prior applications are considered part of (and are incorporated by reference in) the disclosure of this application.

FIELD

Described herein is a process for calibrating a glucose sensor under sterile conditions in a manner which is appropriate for point of use calibration; a calibration unit and glucose sensor kit including the calibration unit as well as a glucose sensor probe; and a process for the preparation of a sterile calibration unit.

BACKGROUND

The usual aim in developing a chemical sensor or biosensor is to produce a signal, which is proportional to the concentration of a specific chemical or set of chemicals (analyte). The sensor usually has two main components, a chemical or biological part that reacts or complexes with the analyte in question (ideally specifically) to form new chemical or biological products or changes in energy that can be detected by means of the second component, a transducer. The chemical/biological component can be said to act as a receptor/indicator for the analyte. A variety of transduction methods can be used including electrochemical (such as potentiometric, amperometric, conductimetric, impedimetric), optical, calorimetric and acoustic. After transduction the signal is usually converted to an electronic digital signal.

Since the signal generated by the chemical/biological reaction with the analyte is usually dependent not only on the concentration of the analyte but also on the characteristics of the sensor itself, such sensors usually require calibration before they can be utilised quantitatively. The way in which the signal varies with the analyte concentration determines the shape of the calibration curve (signal versus analyte concentration) and may define the number of calibration points. Typical calibration curves can be straight line, exponential, s-shaped etc and the principal of calibration applies to all methodologies of transduction for chemical or biological sensors.

Calibration of sensors with an invasive medical application has its own set of specific issues. Invasive or implantable medical sensors are to be presented to the patient in a sterile condition, and are often single use, disposable devices. Ideally, the sensor should be calibrated just before its use since some sensor characteristics that can affect the calibration curve vary with time (ageing effect). It is often the case that the time between sensor manufacture and use can be many months, so calibration at the point of manufacture can lead to inaccuracies in the end result. This means that the attendant clinician or nurse will be required to perform the calibration whilst maintaining sterility of the sensor. Additional constraints applied by the clinician/nurse are that the calibration process should be simple to perform, ideally invisible to the person performing the calibration, and be quickly completed (preferably in less than 10 minutes).

Calibration of many currently available medical sensors requires the clinician/nurse to carry out a number of specific steps which can lead to errors or inaccuracies in the measurement if the process is not followed correctly. There is therefore a need for a more simple calibration process, useful in connection with invasive or implantable sensors, which fulfils the above discussed requirements.

Sterilisation of such devices can also present difficulties. The sterilisation process is typically carried out at the point of manufacture to avoid difficulties with poor or incomplete sterilisation procedures at a hospital or clinic, and to save time on behalf of the clinician or nurse. In the case of glucose, however, glucose-containing solutions have been found to degrade on sterilisation with either heat or gamma-radiation. Thus, the pre-sterilisation of such solutions at manufacture must be avoided. Glucose can instead be provided in solid form, since in this state sterilisation can be carried out without causing degradation. However, the user is then required to make up the required glucose-containing calibration solutions at the point of use. This adds additional steps to the procedure and can be time-consuming. For example over 45 minutes may be required to ensure that glucose has fully dissolved and equilibrated in the solution.

Further, there is a need to maintain sterility during the calibration, a factor which is difficult to achieve given the differing sterilisation processes which may be needed for different parts of the calibration unit and sensor. Sterility will be lost if the process requires the user to break open sterile packages in order to complete calibration.

There is therefore particularly a need for a means of calibrating a glucose sensor which can be carried out under sterile conditions, without loss of sterility during the process, and which can be carried out in a short time.

SUMMARY

Provided herein is a process for calibrating a glucose sensor in a sterile environment, the glucose sensor comprising a sensing probe for detecting glucose, the process comprising:
(i) providing a calibration unit comprising (a) at least a first and a second sterile calibration fluid, each calibration fluid having a different concentration of glucose, (b) a sensing zone, a sensing region of the probe of the glucose sensor being located within the sensing zone, and (c) a waste chamber for collecting used calibration fluid;
(ii) providing the first calibration fluid to the sensing zone such that the fluid is in contact with the sensing region, and determining the sensor output;
(iii) flushing the first calibration fluid to the waste chamber;
(iv) providing the second calibration fluid to the sensing zone such that the fluid is in contact with the sensing region, and determining the sensor output;
(v) using the sensor output readings to calibrate the glucose sensor; wherein the calibration process is carried out under sterile conditions.

Typically, said process is a process for calibrating an invasive fibre optic glucose sensor containing a fluorescent glucose indicator system, the sensor probe being adapted to detect glucose in vivo.

Also provided is a glucose sensor kit comprising a sensing probe for detecting glucose and a calibration unit, the calibration unit comprising:
- a sensing zone having at least one inlet and at least one outlet, a sensing region of the probe being located in the sensing zone;
- a first calibration chamber containing a first sterile calibration fluid, the first calibration chamber being connected to, or adapted for connection to, an inlet to the sensing zone;
- a second calibration chamber containing a second sterile calibration fluid having a glucose concentration different from that of the first calibration fluid, the second calibration chamber being connected to, or adapted for connection to, an inlet to the sensing zone;
- at least one fluid propulsion means, e.g. manual or automated propulsion means, for propelling calibration fluid from the calibration chambers to the sensing zone;
- a waste chamber arranged to collect used calibration fluid which is flushed out of the sensing zone;

the glucose sensor kit being arranged to carry out calibration of the sensor under sterile conditions.

Typically, the sensing probe comprised in said kit is part of an invasive fibre optic glucose sensor containing a fluorescent glucose indicator system, and the sensor probe is adapted to detect glucose in vivo.

The process and kit described herein therefore provide for sterile calibration, which can be completed in a short timescale and whilst maintaining sterility. This is particularly beneficial where calibration is carried out at point-of-use. In particular, where previous sterile calibration processes relied upon calibration solutions being prepared by the user, the calibration methods, systems, and devices provided herein can avoid this time-consuming step by providing the glucose solutions in ready to use form. This means that the user can directly provide the solutions to the sensing zone of the calibration unit, and a reading can immediately be taken. Significant time savings in the calibration carried out by the user can be made.

The ready-to-use sterile glucose calibration solutions can be prepared by a process comprising the steps:

(i) providing glucose in solid form in a first mixing chamber, and water or an aqueous solution in a second mixing chamber;

(ii) sterilising the first and second mixing chambers by use of heat or irradiation;

(iii) mixing the contents of the first and second chambers to provide a first, sterile glucose-containing calibration fluid;

(iv) providing at least a portion of the first calibration fluid to a first calibration chamber, whilst maintaining sterility of the fluid;

(v) providing at least one further sterile calibration fluid, each further fluid having a glucose concentration different from one another and from the first calibration fluid, the further calibration fluid(s) being provided in one or more further calibration chambers;

(vi) connecting the first and one or more further calibration chambers to a calibration unit such that the calibration chambers are connected to, or adapted for connection to, an inlet to a sensing zone of the calibration unit;

(vii) sterilising the calibration unit using a surface sterilant, said sterilising step being carried out either before or after step (vi), to provide a sterile calibration unit containing at least two sterile calibration fluids.

The above process therefore provides a convenient manufacturing method to provide ready-to-use sterile glucose calibration fluids within a sterile calibration unit. The method described herein requires only simple equipment in order to prepare the sterile glucose containing solutions. This has the advantage that equipment able to withstand sterilisation by heat (e.g. standard autoclaving) can be used, thus providing a simple manufacturing process.

Also provided is a calibration unit for calibrating a glucose sensor comprising:
- a sensing zone having at least one inlet and at least one outlet, the sensing zone being arranged to house a sensing region of a sensing probe of the glucose sensor;
- a first calibration chamber containing a first sterile calibration fluid, the first calibration chamber being connected to, or adapted for connection to, an inlet to the sensing zone;
- a second calibration chamber containing a second sterile calibration fluid having a glucose concentration different from that of the first calibration fluid, the second calibration chamber being connected to, or adapted for connection to, an inlet to the sensing zone;
- at least one fluid propulsion means, e.g. manual or automated propulsion means, for propelling calibration fluid from the calibration chambers to the sensing zone;
- a waste chamber arranged to collect used calibration fluid which is flushed out of the sensing zone; the calibration unit being arranged to carry out calibration of the sensor under sterile conditions.

Typically said calibration unit is suitable for calibrating an invasive fibre optic glucose sensor, said sensor containing a fluorescent glucose indicator system and a sensor probe being adapted to detect glucose in vivo.

DETAILED DESCRIPTION

A glucose kit is described further with reference to the accompanying drawings which serve as an example and are not intended to limit the scope of the invention.

Reference is made herein to sterile calibration fluids and to calibration being carried out under sterile conditions. The term sterile indicates that the fluid or conditions are free from living germs or microorganisms. Sterility as referred to herein can be achieved by standard techniques of sterilisation well-known in the art, for example autoclave, gamma-radiation or chemical sterilisation, e.g. by ethylene oxide.

Glucose Sensor

The calibration process described herein can be used with an invasive (including implantable) glucose sensor, for example a sensor which determines glucose concentration in blood (e.g. intravascular), or in interstitial tissue (e.g. subcutaneous). In some cases, the sensor probe is adapted to detect glucose in vivo. Such sensors are required to be sterile immediately prior to use and accordingly if calibrated at point of use, this should be done without loss of sterility. In some cases, the calibration process is for use with a fibre optic sensor including a fluorescent indicator system. Such sensors and indicator systems are known, for example, from U.S. Pat. No. 6,387,672 and WO 2012/095628. The described calibration process and kit can, however, be used with any type of glucose sensor requiring sterile calibration.

Figure 1:
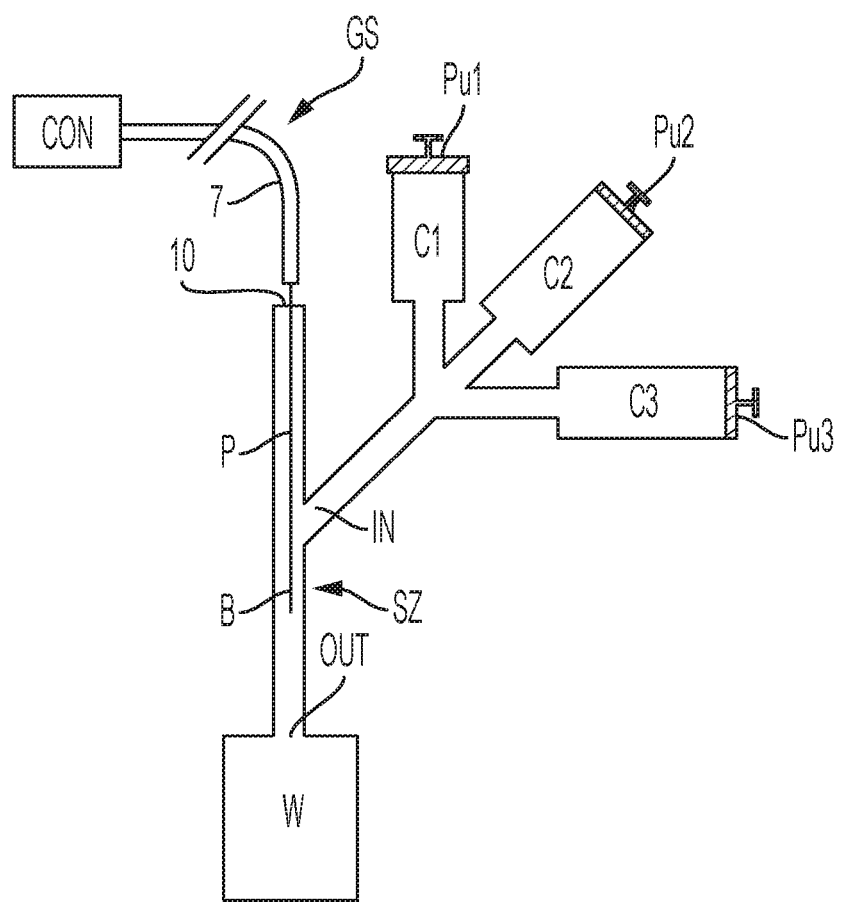
FIG. 1 schematically depicts a glucose sensor kit as provided herein.
Figure 2:
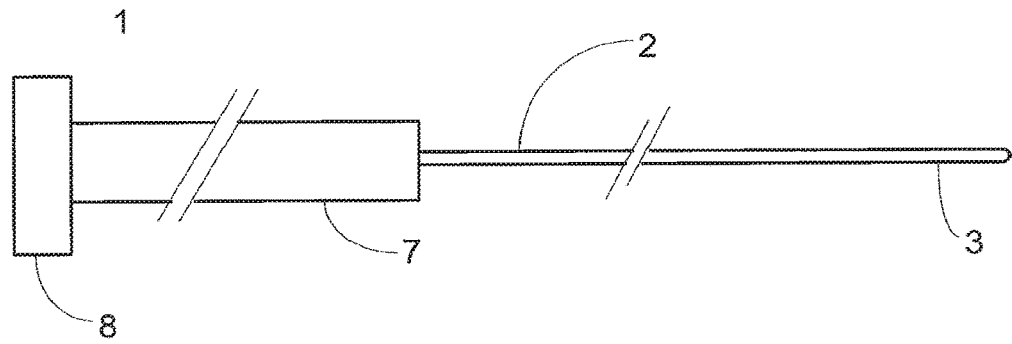
FIGS. 2 and 2a schematically depict a sensor for calibration by the process described herein.
Figure 2A:
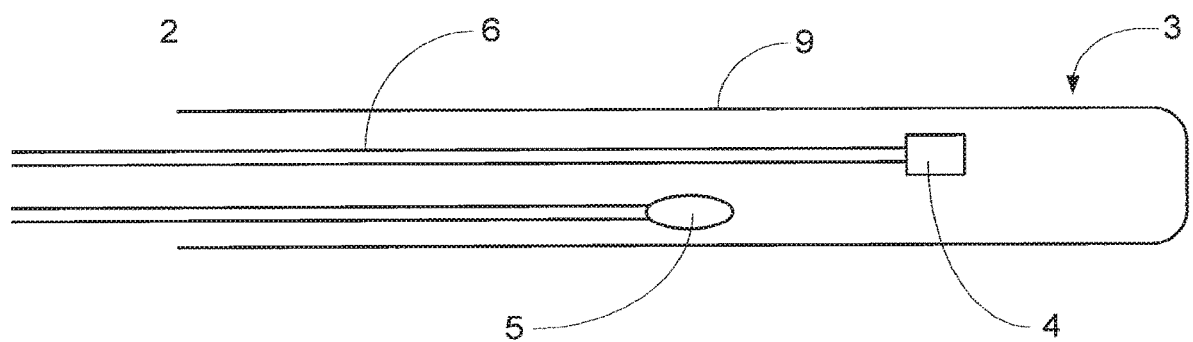

One particular invasive glucose sensor is based on a fibre optic technique and is depicted in FIG. 2. The sensor 1 includes a probe 2 which is adapted for insertion into a patient, for example insertion into a blood vessel through a cannular. The probe includes a sensing region 3, designed to contact a sample to be tested, (depicted in more detail in FIG. 2a) in which the glucose indicator system 4, and typically also a temperature sensor 5, are positioned. The glucose indicating system is immobilised on or in an optical fibre 6, such that a signal emitted by the indicating system is transmitted through the optical fibre. The optical fibre extends through cable 7 to connector 8, which is adapted to mate with a controller (e.g. as depicted in FIG. 1). The controller is typically connected to further optical cable that mates with the connector at one end and at the other bifurcates to connect to (a) an appropriate light source for the optical sensor and (b) a detector for the emitted signal. Electrical connection to the temperature sensor is also provided through connector 8 and appropriate detection equipment is provided by the monitor.

The probe may be provided as a disposable unit, adapted for connection to a non-disposable controller. Thus, for example, the disposable unit may include the probe 2, cable 7 and connector 8. The sensor kit described herein can include a disposable probe unit including the probe, cable and connector, the connector being arranged to optically connect the probe unit to a controller.

The sensing region of the sensor can be surrounded by (or housed in) a membrane 9, which can be haemocompatible, or provided with a haemocompatible coating, and can allow diffusion of glucose from the surrounding blood or body fluid to the indicating system 4.

A suitable indicator system can include a boronic acid compound, e.g. a diboronic acid, acting as receptor and a fluorophore. A boronic acid species can provide the ability to complex with glucose and the fluorescence emission pattern of the fluorophore can be altered in the presence of glucose, which can allow optical detection.

In some cases, the indicator system can be immobilised to the optical fibre in a hydrogel which allows diffusion of water and glucose to the receptor compound. Cross-linked polyacrylamide or polyhydroxyethylmethacrylate (p-HEMA) are examples of hydrogels that can be used.

Calibration Unit

A calibration unit according to one embodiment is depicted in FIG. 1. The calibration unit can include a sensing zone SZ which is arranged to house the sensing region 3 of the probe P of glucose sensor GS. The sensor is depicted in position in the sensing zone in FIG. 1, but the calibration unit may be provided without the probe within the housing. In this case, the probe is separately inserted, typically under sterile conditions. This may be done, for example, by inserting probe 3 through seal 10. Further, FIG. 1 depicts probe 3 connected to cable 7 and ultimately to controller CON. Alternatively, a disposable probe unit including probe 3, cable 7 and connector 8 (not depicted) may be provided, the connector being adapted for later connection to a suitable controller.

The sensing zone SZ can be capable of containing fluid for glucose detection. Thus, the sensing zone can be arranged to contain a calibration fluid whilst a sensor reading is taken using the sensing region 3 of probe P. At least one inlet (IN) and at least one outlet (OUT) can be provided to enable calibration fluids to enter and exit the sensing zone.

In some embodiments the sensor is an invasive glucose sensor. In such embodiments the probe P is configured to detect analyte in a sample while located within the body of a subject (e.g. not merely mounted on tissue such as the subject's skin). However, the calibration unit is typically not used to calibrate the sensor while the sensor is in vivo, because it is typically not desirable to introduce calibration fluid into the body of a subject.

In order to be suitable for calibrating an invasive fibre optic glucose sensor, the calibration unit is typically configured to be removed from the invasive sensor prior to use of the sensor to detect analyte in a sample. Thus, the presence of the calibration unit is typically not required in order for the invasive sensor to perform its function in vivo. Typically, the sensing zone SZ of the calibrator is not the zone in which the sensing region 3 of probe P is located when performing its function in vivo.

The calibration unit can include at least two calibration chambers. As depicted in FIG. 1, three calibration chambers are preferred for calibration of glucose. Glucose has a non-linear calibration curve, so accurate calibration can be carried out by use of at least three calibration fluids, each having a different glucose concentration. The three calibration chambers C1, C2 and C3 can contain, respectively, the three calibration fluids. The glucose content of each calibration fluid is different from the other fluids and is a known, i.e. pre-determined, amount.

In some cases, each calibration fluid is made up of water or an aqueous solution, together with the desired glucose. In some cases, pure water or an isotonic solution is used, to which the desired glucose content is added. For example, concentrations of glucose in the calibration fluids can include zero and concentrations at the upper and lower end of those which are likely to be measured by the sensor. In the example of calibration of a glucose sensor for use with intensive care patients, one calibration fluid typically has a zero concentration, whilst the other calibration fluids typically have concentrations of, for example 5 mmolL$^{-1}$ and 10 mmolL$^{-1}$ respectively. Alternative concentrations could, however, be selected depending on the end use of the sensor.

The order in which the calibration fluids are provided is not critical. In one example, the first calibration fluid has zero glucose content, the second calibration fluid has a glucose concentration of 5 mmoL$^{-1}$ and an optional third calibration fluid has a concentration of 10 mmoL$^{-1}$. In an alternative example, the zero-glucose content calibration fluid is provided as a preliminary calibration fluid (present within the sensing zone prior to calibration as described further herein) and the first and second calibration fluids have non-zero glucose concentrations, e.g. of 5 and 10 mmolL$^{-1}$ respectively.

Each calibration fluid is provided in sterile form. Glucose-containing solutions degrade on sterilisation by heat or gamma-radiation. Thus, the sterile glucose-containing solutions can be prepared by the process described below.

Each calibration chamber can include sufficient calibration fluid to fill sensing zone SZ sufficient for sensing to be carried out. In one aspect, the calibration fluid itself can be used to flush out any previous, used calibration fluid present in the sensing zone. In this case, the volume of fluid can be sufficient to fully purge the sensing zone of the used fluid. The volume used can depend on the volume of the sensing zone itself as well as, for example, the inlet. Suitable volumes of calibration fluid are, for example, at least 1 mL, for example at least 2 mL or at least 5 mL.

The calibration chambers C1, C2 and C3 are, in FIG. 1, simultaneously connected to an inlet IN to the sensing zone.

Alternative embodiments are also envisaged, however, in which the calibration chambers are not simultaneously connected to the inlet. For example, the calibration chambers may be provided in a cartridge, which can be rotated, or translated, in order to move each calibration chamber in turn into a position in which it is connected with the inlet. A one-way valve (not depicted) may be provided to control fluid exiting the calibration chamber(s) and to prevent cross-contamination between chambers C1, C2 and C3.

Fluid propulsion means, e.g. a pump, can be provided to propel calibration fluid into the sensing zone. Any suitable means for transferring calibration fluid may be used. For example, a simple plunger as depicted at Pu1, Pu2 and Pu3 which pushes calibration fluid out of chamber C1, C2 or C3 respectively into the sensing zone. Alternative means include other types of pump, or a compression zone at the distal end of the calibration chamber which, when compressed, forces fluid out of the chamber (e.g. as a pipette). FIG. 1 depicts one plunger per calibration chamber. However, a single propulsion means may be provided, for example in the case where the calibration fluids are provided in a cartridge as mentioned above. The propulsion means may be automated or manual.

After a sensor reading has been taken, calibration fluid can be flushed out of the sensing zone via outlet OUT to waste chamber W. The waste chamber can be separated from the sensing zone by a one-way valve (not depicted) to prevent cross contamination into the sensing zone. Calibration fluid may be extracted from the sensing zone using separate extraction means, for example by creating a reduced pressure area in the waste chamber. This can be achieved, for example, by use of a pump, e.g. by extending a plunger provided in waste chamber W to expand the volume of the chamber. In some cases, separate extraction means are not provided and instead calibration fluid is flushed out of the sensing zone by the ingress of the next fluid for testing. Thus, for example, once a sensor reading has been taken for the first calibration fluid, the second calibration fluid can be provided to the sensing zone, this forcing out the first calibration fluid to the waste chamber.

The unit, including the calibration fluids, can be provided in sterile form. Thus, the sensor probe and all inner surfaces of the calibration unit which may come into contact with the calibration fluids can be sterile, ensuring that the probe maintains sterility ready for use. Sterility can be provided by use of the preparation process described further herein, which leads to a sealed, sterile calibration unit. The unit can be adapted such that calibration can be carried out without breaking the seal of the calibration unit and thus maintaining sterility. A seal (e.g. 10) may be opened after calibration to access the sensor probe for immediate use.

The calibration unit may include a controller such as a microprocessor, arranged to calibrate the sensor using at least two and typically three sensor output readings. Alternatively, the controller of the sensor itself may be used to carry out the calibration process. In the latter case, the calibration unit, or disposable sensor probe, may contain information, for example on precise glucose concentration and volume of the calibration fluids, which is readable by the controller (e.g. in bar code form).

As depicted in FIG. 1, all calibration fluids can be present in the calibration chambers C1, C2 and C3. However, glucose sensors often include a hydrogel, for example a hydrogel may be used to immobilise the indicator system. Such sensors are advantageously maintained in hydrated form. In an alternative aspect, therefore, one of the calibration fluids (typically a preliminary calibration fluid having zero-glucose content) is provided to the sensing zone at the point of manufacture, for example immediately after sterilisation. This can ensure that a sensing region of the probe, which is present in the sensing zone, is hydrated during shipping and storage. This can further reduce the time of calibration since the initial sensor output reading can be taken without the need to carry out any further preliminary steps.

Calibration Process

The calibration can be carried out by providing calibration fluid, e.g. from C1, to the sensing zone via application of pressure, e.g. from plunger Pu1. The sensor output can then be determined. In the case that calibration fluid (typically preliminary calibration fluid which does not contain glucose) is provided to the sensing zone prior to storage, this step can be carried out at the point of manufacture. The calibration process therefore can be initiated with preliminary calibration fluid already present within the sensing zone and the first step in the calibration process can therefore determining sensor output of the preliminary calibration fluid.

The used calibration fluid can then be flushed from the sensing zone. This may be achieved by creating a reduced pressure in the waste chamber which draws calibration fluid out of the sensing zone. In some cases, however, no separate step of removing the used calibration fluid is carried out. Instead, Pu2 can be depressed forcing the next calibration fluid to enter the sensing zone, the entry of the next calibration fluid forcing used calibration fluid out of the sensing zone. A second sensor output reading can then be taken.

In some cases, these steps can be repeated with a further calibration fluid, thus providing three sensor output readings which can be used to calibrate the sensor. In some cases, at least two sensor output readings are used to calibrate the sensor. In some cases, at least three sensor output readings are used to calibrate the sensor. The various steps of the calibration process can be automated.

Invasive sensors can, in some cases, operate in a temperature range of 35-39 C. However, calibration is normally carried out at room temperature. In some cases, sensors calibrated with calibration methods, systems, and devices provided herein can be sensitive to temperature variation, in which case a calibration curve generated at room temperature may be shifted to a different set of values at, say, 37 C.

The sensor probe described herein may contain a temperature sensor (5 of FIG. 1), such that the temperature at which calibration is carried out can be determined. If the shift of the calibration curve with temperature for any particular sensor is known, following generation of the calibration curve as described above the curve can be shifted as necessary to account for the difference in temperature from that measured by the sensor during calibration to 37 C. Alternatively, a heating element (not depicted) may be provided to control the calibration temperature. For example, the heating element may increase the temperature within the calibration unit to 37 C prior to calibration. Alternatively, the temperature may be varied during calibration in the manner described in WO2012/164268.

The resulting calibrated sensor may be used to determine the glucose content of a sample. In some cases, the user accesses the sensor by removal of a seal (e.g. 10) or opening the sealed packaging of the calibration unit. The sensing region of the probe can then be inserted into the sample and the glucose content of the sample determined. The sample may be an in vitro sample such as a blood or plasma sample, or alternatively the probe is inserted invasively into a human or animal subject, for example into a blood vessel via a cannular. The sensor may then be used to determine the blood glucose content.

Preparation of Sterile Calibration Unit

Figure 3:
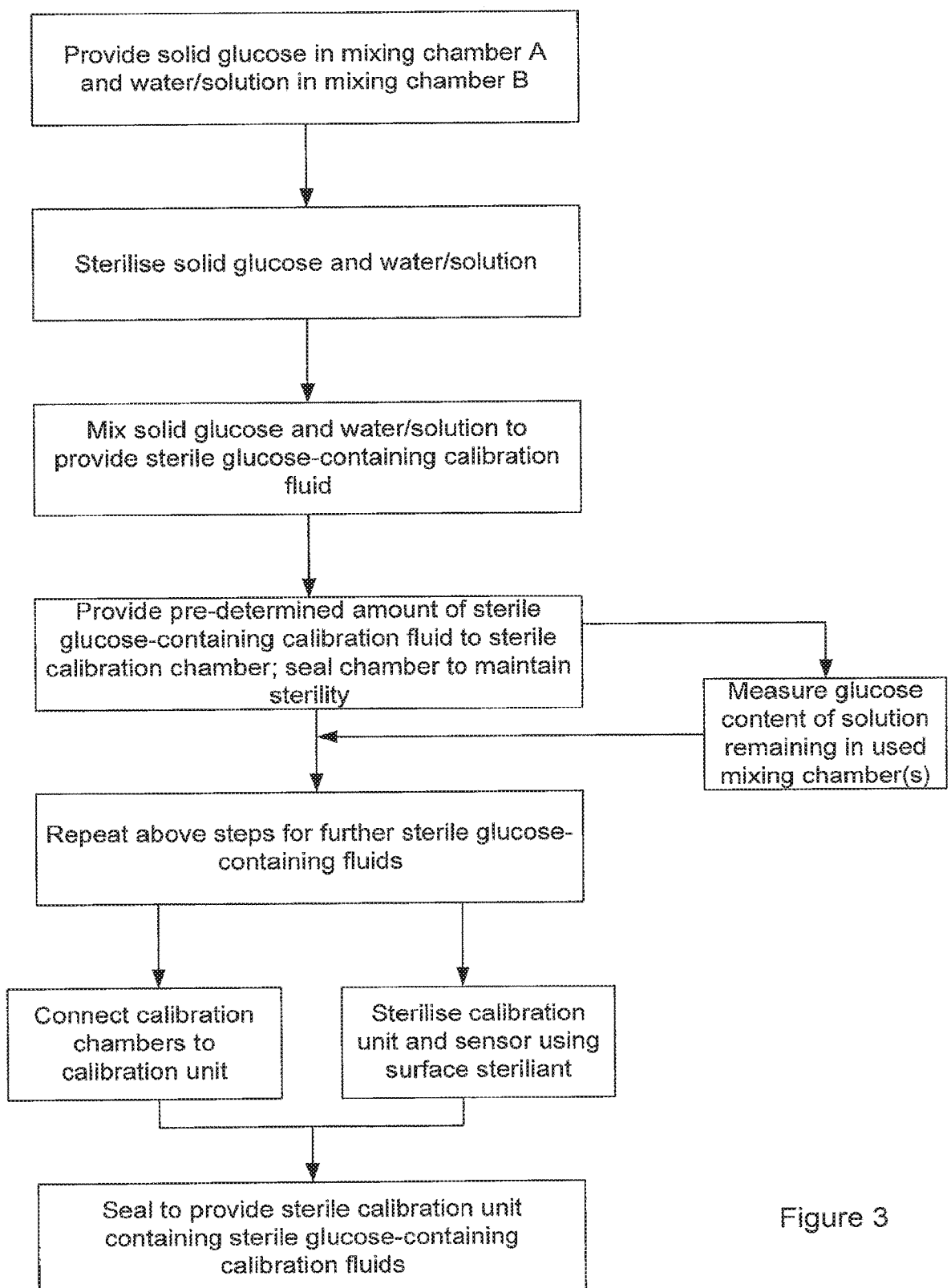
FIG. 3 provides a flow chart depicting the process for preparing a sterile calibration unit as described herein.
Figure 4:
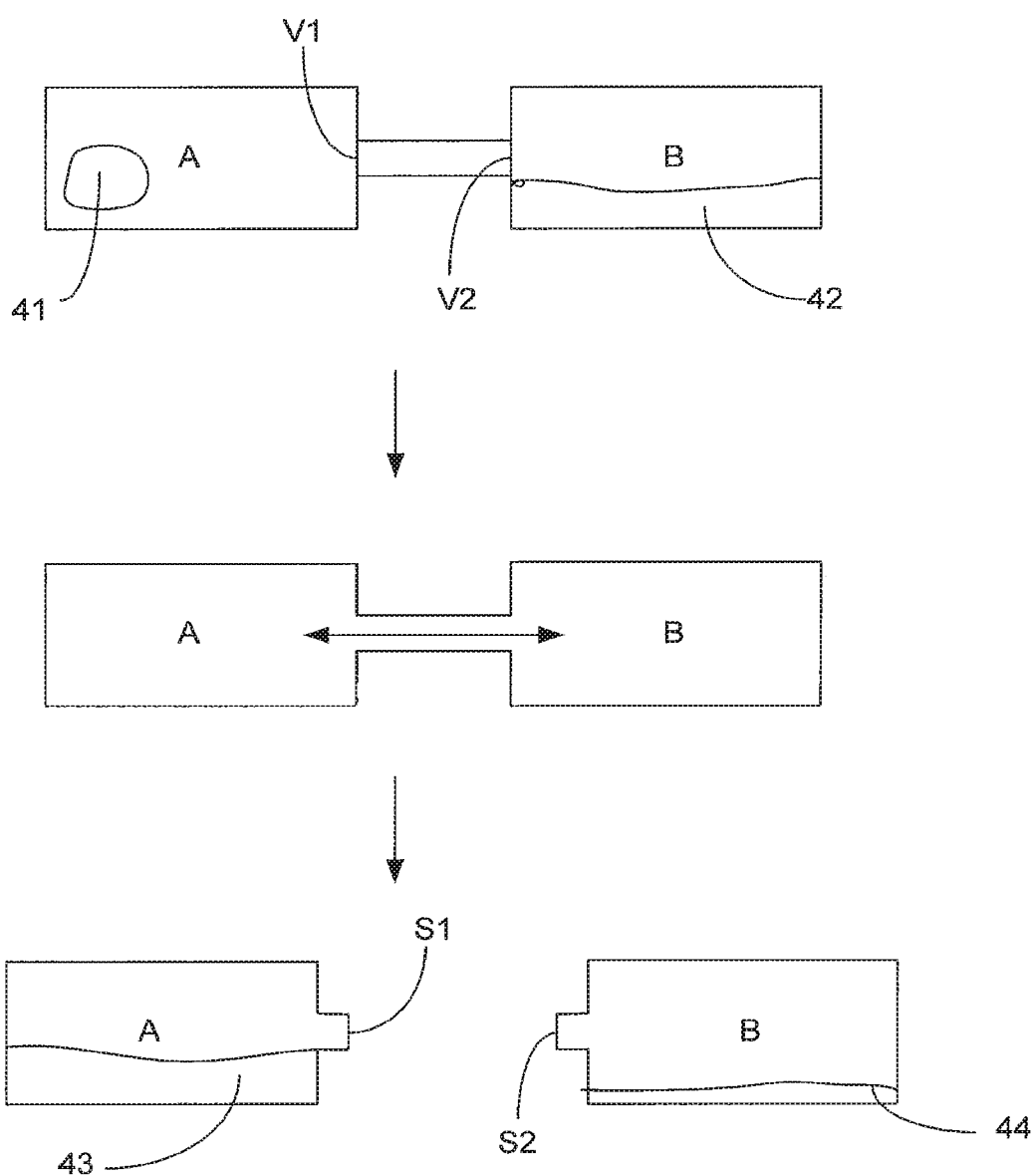
FIG. 4 schematically depicts the process for preparing a sterile calibration unit as described herein.

The process for preparing a sterile calibration unit can be carried out according to the steps depicted in the flow-chart of FIG. 3 and in schematic steps in FIG. 4. In some cases, solid glucose 41 and water, or an aqueous solution (e.g. an isotonic solution) intended to form the basis of the calibration fluid, 42 are provided to separate mixing chambers, A and B in a first step. Chambers A and B can be connected in such a manner that the contents of the chambers are separated during sterilisation (e.g. to prevent unwanted migration of the contents of the chambers during sterilisation), but can be mixed after sterilisation. For example, chamber A may be connected to, or adapted for connection to, an inlet to chamber B (or vice versa). In some cases, the chambers can be separated by a removable seal such that they are in fluid communication with one another on removal of the seal, e.g. the chambers may be separated by one or more valves V1, V2, or removable stoppers, during sterilisation. The chambers being in fluid communication with one another means that the water/solution 42 can flow between the two chambers once any stopper/valve means used is opened.

Sterilisation is carried out with the materials in separate mixing chambers A and B. Suitable sterilisation means include heat, e.g. standard autoclaving, or gamma-radiation. Heat, e.g. standard autoclaving is preferred. Following sterilisation, mixing is carried out, e.g. by opening a valve between the two mixing chambers or removing a stopper between the two chambers. Mixing means may be provided. For example, a pump (e.g. a plunger) may be provided to each mixing chamber so that mixing occurs by repeated pumping of solution from one chamber to the other. Alternative mixing means are, however, envisaged, provided that mixing occurs without loss of sterility. Mixing may be manual or automated.

All or a portion of the sterile calibration fluid produced can be transferred to a calibration chamber. This may be a separate calibration chamber which has been pre-sterilised. More conveniently, however, mixing chamber A or B is used as the calibration chamber. FIG. 4 depicts mixing chamber A as the calibration chamber. The chamber is, if necessary, sealed (stopper Si) to maintain sterility and to ensure calibration fluid remains within the chamber. If the chamber is not sealed, attachment to the calibration unit can be carried out under sterile conditions.

If only a portion of the calibration fluid is provided in the calibration chamber, remaining calibration fluid can be left in one or more mixing chambers, e.g. 44 in mixing chamber B of FIG. 4. Optionally, the glucose content of the remaining calibration fluid is determined. Since the glucose concentration of the remaining fluid is identical to that of the calibration fluid, this can give a precise figure for the calibration fluid glucose content, which does not rely on calculating the concentration from the amount of solid glucose and liquid volume supplied. This has the benefit that inaccuracies in the dispensing of solid glucose or liquid will not affect the calibration. The resulting glucose concentration may be provided to the calibration unit as a part of the information required for calibration and may be used in the calibration as the glucose concentration of the calibration fluid.

The above steps can thus provide a glucose-containing calibration fluid in sterile form which can be used in the calibration process described herein. In some cases, at least two glucose-containing calibration fluids are required for an accurate calibration of a glucose sensor. Thus, the above steps can be repeated, using a different amount of glucose 41, and/or a different volume of water/solution 42, to provide a further calibration fluid having a different glucose concentration. A glucose-free solution can also be provided. A glucose-free solution may be sterilised by direct application of heat or gamma-radiation to the calibration chamber containing the calibration fluid.

The various parts of the calibration unit, including the calibration chambers, can be placed within a sealed packaging, ready for sterilisation. The sensor probe, e.g. a disposable probe unit, can also be at least partly contained within the sealed packaging. In some cases, at least the sensing region of the probe is within the sealed packaging, whilst the connector 8 remains outside the packaging since it does not require sterilisation. Seal 10 may be provided around the probe to ensure no loss of sterility. The packaging itself can be gas-permeable to allow penetration of the sterilant. The entire unit can then be sterilised using a surface sterilant such as ethylene oxide.

Assembly of the various parts of the calibration unit may be carried out before or after sterilisation. In some cases, assembly of the unit occurs after sterilisation, within the sealed, sterile packaging in order to maintain sterility. Thus, attachment of the calibration chambers, e.g. by attachment to inlet IN, may be carried out before or after sterilisation. Stoppers 51 may be removed from the calibration chambers prior to attachment. In some cases, the stoppers may be in the form of valves which can be opened at the appropriate time during calibration. Similarly, assembly of the sensor probe, e.g. the disposable probe unit, into the calibration unit by insertion of the sensing region of the probe into the sensing zone, may be carried out before or after sterilisation. If before, the calibration unit can be gas permeable to allow penetration of the sterilant to the sensor probe.

The calibration unit may be provided alone, or with the sensor probe (e.g. provided as a disposable probe unit) in place in the form of a sensor kit. In some cases, the sensor probe is in place in the calibration unit in order to avoid any loss of sterility by the user having to expose a sensor probe and insert it into the calibration unit. Sealing the kit may be conveniently achieved by use of a removable seal which the user can peal away to remove the sensor once calibration has been carried out.

The preparation of the unit may optionally include an additional step of providing a zero-glucose content calibration fluid to the sensing zone. This can ensure that a sensor probe present in the sensing zone remains hydrated during storage and reduces the time for calibration by the end user.

The invention claimed is:

1. A process for preparation of a calibration unit for calibrating a sensor surrounded by a membrane, comprising the steps:

providing an analyte in solid form in a first mixing chamber, and water or an aqueous solution in a second mixing chamber;

sterilizing the first and second mixing chambers by use of heat or irradiation;

mixing contents of the first and second chambers to provide a first, sterile analyte-containing calibration fluid;

providing at least a portion of the first calibration fluid to a first calibration chamber, whilst maintaining sterility of the fluid;

providing at least one further sterile calibration fluid, each further fluid having an analyte concentration different from one another and from the first calibration fluid, the at least one further calibration fluid being provided in one or more further calibration chambers;

connecting the first and one or more further calibration chambers to the calibration unit such that the first and one or more further calibration chambers are connected to, or adapted for connection to, an inlet of a sensing zone of the calibration unit;

sterilizing the calibration unit using a surface sterilant such that the calibration unit contains at least the first calibration fluid and the at least one further calibration fluid.

2. The process according to claim 1, further comprising sealing the first calibration chamber in order to maintain sterility.

3. The process according to claim 1, further comprising providing a sterile calibration fluid having zero analyte concentration.

4. The process according to claim 1, wherein the first mixing chamber or the second mixing chamber forms the first calibration chamber.

5. The process according to claim 1, wherein a portion of the first calibration fluid is provided in the first calibration chamber and remaining fluid is provided within either the first or the second mixing chamber, and wherein the process further comprises determining an analyte concentration of the remaining fluid.

6. The process according to claim 1, further comprising providing a sensor probe for detecting the analyte, wherein a sensing region of the sensor probe is housed within the sensing zone of the calibration unit.

* * * * *